(12) United States Patent
Termanini

(10) Patent No.: US 10,595,886 B2
(45) Date of Patent: Mar. 24, 2020

(54) ARTHROSCOPIC SHOULDER ARTHROPLASTY AND METHOD THEREOF

(71) Applicant: Zafer Termanini, Port Saint Lucie, FL (US)

(72) Inventor: Zafer Termanini, Port Saint Lucie, FL (US)

(73) Assignee: Joint Innovation Technology, LLC, Boca Raton, FL (US)

( * ) Notice: Subject to any disclaimer, the term of this patent is extended or adjusted under 35 U.S.C. 154(b) by 0 days.

(21) Appl. No.: 15/911,128

(22) Filed: Mar. 4, 2018

(65) Prior Publication Data

US 2019/0269423 A1    Sep. 5, 2019

(51) Int. Cl.
*A61B 17/17*    (2006.01)
*A61B 17/14*    (2006.01)
(Continued)

(52) U.S. Cl.
CPC ........ *A61B 17/1778* (2016.11); *A61B 17/142* (2016.11); *A61B 17/144* (2016.11); *A61B 17/15* (2013.01); *A61B 17/1633* (2013.01); *A61B 17/1659* (2013.01); *A61B 17/1684* (2013.01); *A61F 2/30749* (2013.01); *A61F 2/4003* (2013.01); *A61F 2/4014* (2013.01); *A61F 2/4081* (2013.01); *A61F 2/4612* (2013.01); *A61F 2/4637* (2013.01);
(Continued)

(58) Field of Classification Search
CPC ...... A61F 2/30749; A61F 2/40; A61F 2/4014; A61F 2/4081; A61F 2/4612; A61F 2/4003; A61F 2002/4022; A61F 2002/4085; A61F 2002/30476; A61F 2002/4018; A61F 2002/4011; A61F 2002/4007; A61F 2002/4658; A61B 17/1778; A61B 17/142; A61B 17/15; A61B 17/1633; A61B 17/1659; A61B 2090/061; A61B 90/06; B25H 7/04; G01B 5/00; G01B 5/04; G01B 11/06; G01B 11/14; G01B 2003/1089; G01B 3/1084; G01B 7/14; G01B 21/042; G01B 21/04; B23Q 3/183; B23Q 9/0042
USPC ........ 623/19.11–19.14; 606/80; 33/520, 644, 33/666, 670–677
See application file for complete search history.

(56) References Cited

U.S. PATENT DOCUMENTS

| | | | |
|---|---|---|---|
| 597,915 A * | 1/1898 | Roosa ..................... | B25D 5/02 33/675 |
| 4,550,450 A * | 11/1985 | Kinnett ..................... | A61F 2/40 623/20.11 |

(Continued)

OTHER PUBLICATIONS

International Search Report for corresponding application PCT/US2019/020299 dated May 22, 2019.

*Primary Examiner* — David W Bates
*Assistant Examiner* — Marcela I Shirsat
(74) *Attorney, Agent, or Firm* — Norris McLaughlin, PA

(57) ABSTRACT

A novel method and instrumentation for insertion of humeral and glenoid total shoulder implant using arthroscopic visualization for bony preparation as well as insertion of components through small incisions. Mini instruments and cannulated guides and reamers are used in order to perform the procedure under direct arthroscopic visualization. For ease of insertion, the components are inserted separately and assembled in situ. Securing the humeral components in place is accomplished with bicortical screw transfixing the central peg of component.

11 Claims, 15 Drawing Sheets

(51) Int. Cl.
*A61B 17/15* (2006.01)
*A61B 17/16* (2006.01)
*A61F 2/40* (2006.01)
*A61F 2/30* (2006.01)
*A61F 2/46* (2006.01)

(52) U.S. Cl.
CPC .......... *A61F 2002/305* (2013.01); *A61F 2002/30329* (2013.01); *A61F 2002/30476* (2013.01); *A61F 2002/30574* (2013.01); *A61F 2002/4018* (2013.01)

(56) References Cited

U.S. PATENT DOCUMENTS

| | | | | |
|---|---|---|---|---|
| 4,893,619 | A * | 1/1990 | Dale | A61B 17/15 606/82 |
| 4,964,865 | A * | 10/1990 | Burkhead | A61F 2/40 623/19.11 |
| 6,494,913 | B1 | 12/2002 | Huebner et al. | |
| 8,753,402 | B2 * | 6/2014 | Winslow | A61B 17/1684 623/19.14 |
| 2003/0149485 | A1 | 8/2003 | Tornier | |
| 2005/0043805 | A1 * | 2/2005 | Chudik | A61B 17/1778 623/19.14 |
| 2005/0107882 | A1 | 5/2005 | Sone et al. | |
| 2009/0192621 | A1 | 7/2009 | Winslow et al. | |
| 2014/0107652 | A1 * | 4/2014 | Walker | A61B 17/15 606/81 |
| 2016/0235540 | A1 * | 8/2016 | Termanini | A61F 2/38 |

* cited by examiner

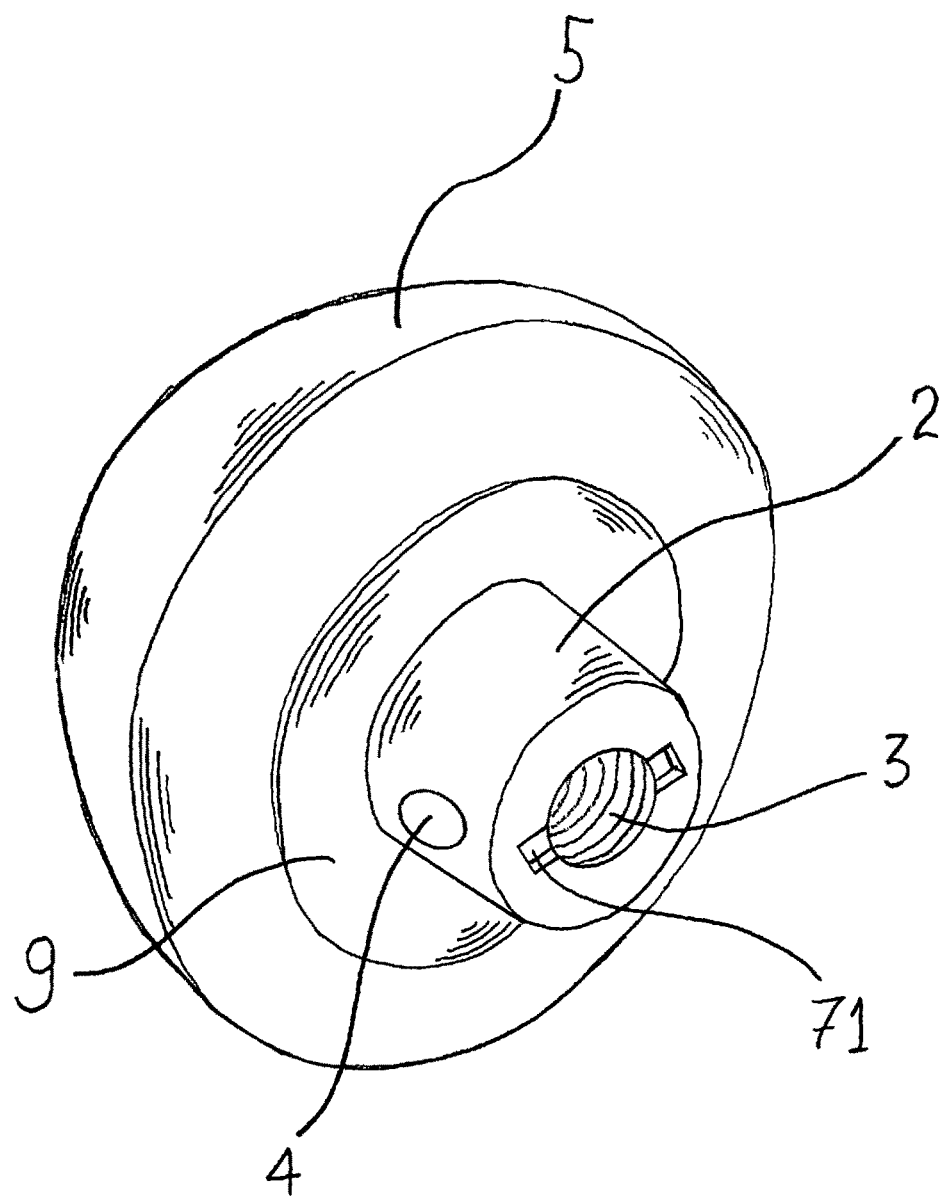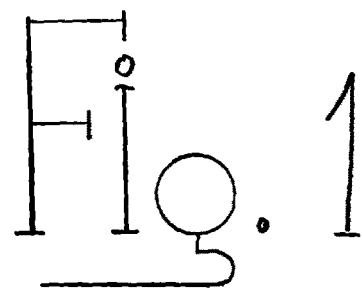

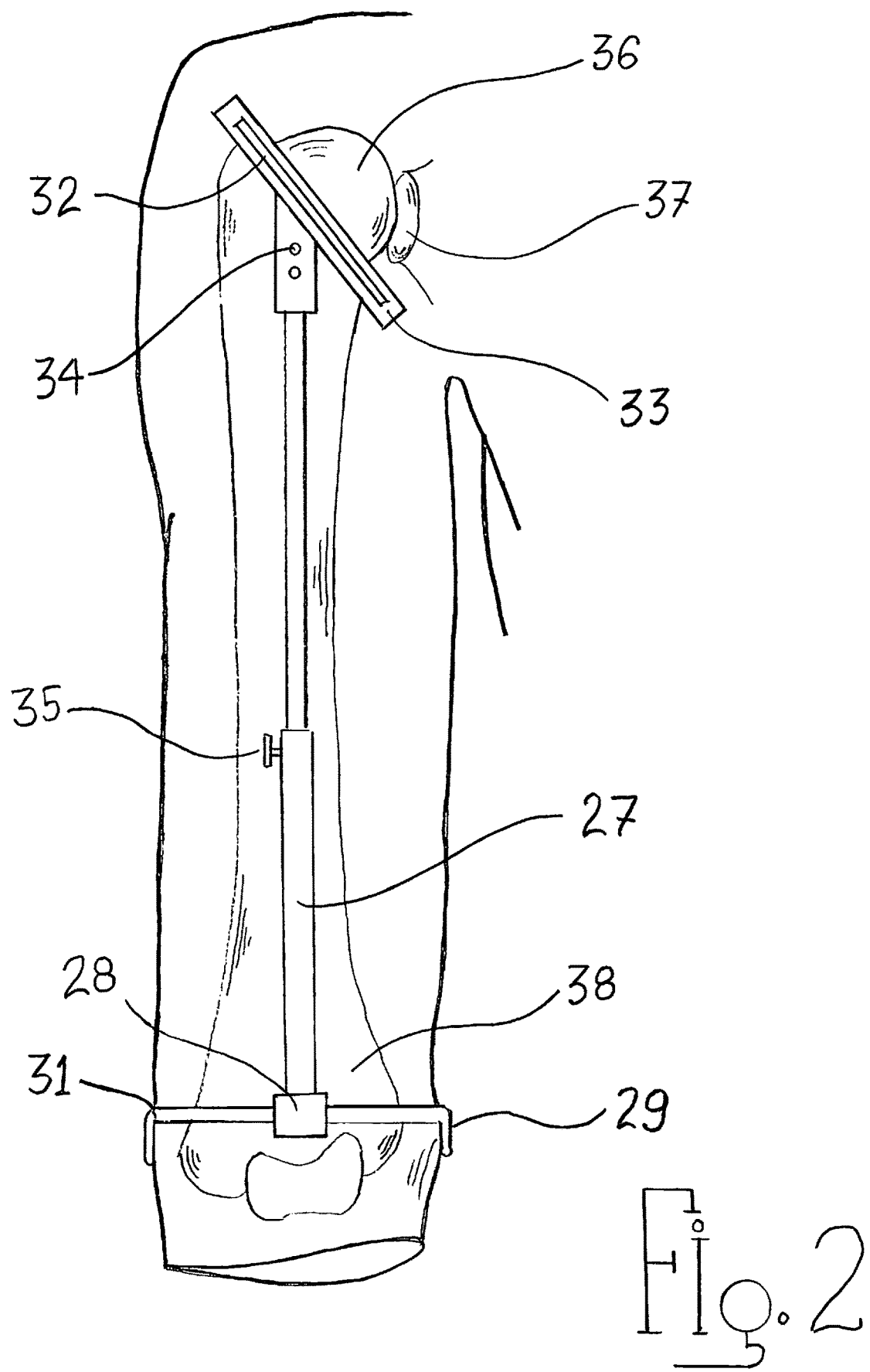

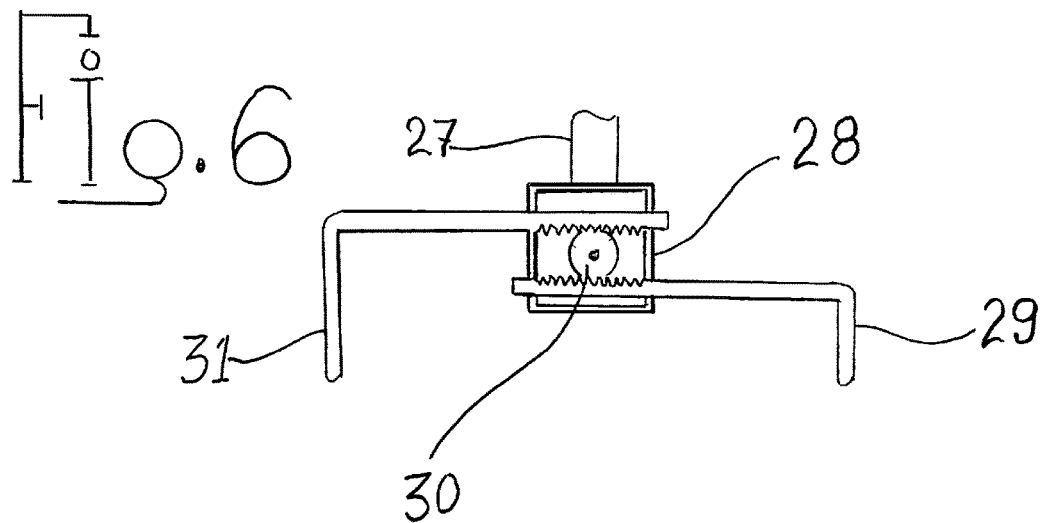
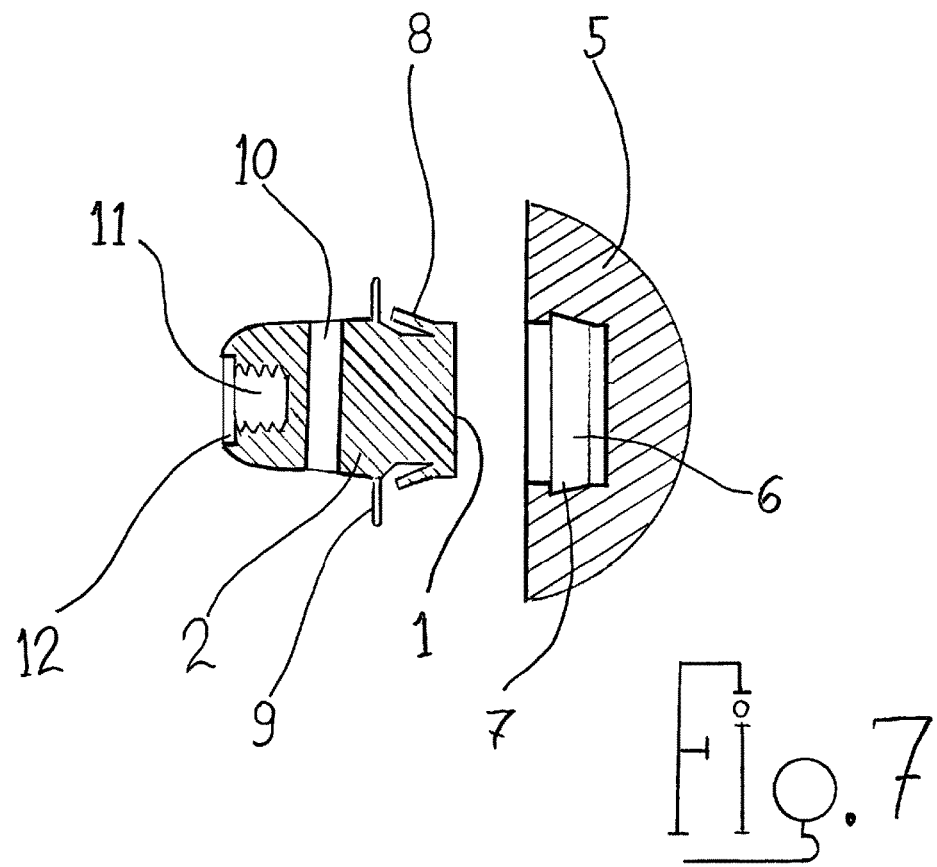

ARTHROSCOPIC SHOULDER ARTHROPLASTY AND METHOD THEREOF

FIELD OF THE INVENTION

The present invention relates to the use of patient specific shoulder implants and in particular to the use of instrumentation and guides for allowing the insertion of the implant component arthroscopically.

BACKGROUND OF THE INVENTION

Shoulder joint replacement has been in use for many decades. The articular surfaces of the shoulder joint include a ball and a socket which may be damaged by trauma or degenerative disease. Pain and limitation of movement will require a replacement of the articular surfaces using a hemispherical humeral component and a shallow glenoid component. Damages to the rotator cuff and supporting structures will require the use of reverse shoulder implant, where the geometry of the components is reversed, and the humeral component is designed as a cupule while the hemispherical ball is attached to the glenoid plate.

However, the surgical procedure for the insertion of the prosthetic component requires significant surgical exposure that will unduly damage local anatomical structures such as surrounding muscles and adjacent tendon tendons. Said damage will impose longer healing period and require extensive postoperative physical therapy. However, both anatomical shoulder implants as well as more recent reverse implants are traditionally inserted through conventional surgical approach. Traditionally, the proximal humerus is reamed to allow for insertion of the stem of the humeral component. However, the existence of prior trauma and deformity of the proximal humerus preclude the use of implant with humeral stem. More recently, stem free or stemless humeral component are designed and used but remain bulky and require insertion through a conventional extensive surgical approach. The shoulder joint is anatomically a distraction joint as opposed to the hip knee and ankle joints which are weight bearing and compression joints. In the shoulder joint, compression forces are limited to lifting heavy objects when the arm is in the horizontal position. Conventionally used glenoid polyethylene components are known to flow and become loose leading to osteolysis.

BRIEF SUMMARY OF THE INVENTION

The purpose of the present invention is to present a novel method and surgical technique providing improved instrumentation for insertion of total shoulder implant components arthroscopically. Therefore, minimizing damage to the surrounding muscles and supporting ligaments and tissues. Therefore, the object of this invention is to provide a surgical method for insertion of the humeral and glenoid implant components using arthroscopic techniques using stab wounds and minimal surgical incision. Minimal incisions are used to perform the initial steps of the procedure. An arthroscope is introduced superiorly and laterally in the usual conventional technique to visualize the anterior surface of the proximal humerus. Initially the humeral head is transected, which will debulk the joint and provide a working space into the shoulder joint. An external cutting guide having a slot of 50° inclination is secured to the humerus using a pin inserted percutaneously below the surgical neck of the humerus. Said external guide is aligned along the anterior surface of the arm. A mini-reciprocating saw is inserted anteriorly through a small anterior skin incision and passed through the guiding slot of the external guide and osteotomy of the head is carried out. To facilitate the extraction of the head, it can be fragmented and removed in pieces. A reciprocation saw, or high-speed burr may be used for the fragmentation under direct arthroscopic visualization. These tools are redesigned for use through the slotted guide. In the preferred embodiment of this invention, the glenoid component is metallic. The glenoid component having a rimmed metallic base to be attached to the reamed and prepared glenoid surface with a central peg and two large cancellous screws. The polished metallic articular glenoid component will be subsequently snapped in and secured in the recess of glenoid base plate by multiple locking tabs.

The next step is to prepare the humeral head to receive the humeral implant. A mechanical center locator device is inserted through the first small anterior skin incision that will allow to locate the center of the humeral cut surface under direct visual supervision of the operating surgeon through the arthroscope. Said device provide an attachment for outrigger to be attached to it. Said outrigger will allow the insertion of guide pin through a stab wound of the lateral surface of the shoulder and penetrate the lateral cortex of the humerus allowing it to exit through the center of the cut surface of the humeral head. A cannulated shaft is inserted onto the guide wire. A small circular boring reamer will be introduced over the central guidewire, which will allow to make a cylindrical central recess in the humeral cut surface that will accept the central metallic peg of the humeral component. The central peg of said humeral implant has a threaded central hole which will be threaded over treaded end of the compressor rod. Said rod having a gliding sleeve that will allow the use of an outrigger for the purpose of guiding a drill for making a hole through the anterior surface of the proximal humerus for securing the metallic component of the humeral implant using a fixation screw.

Under direct vision, a central guide wire is inserted into the center of the glenoid fossa and a circular reamer is inserted onto the central guide wire and used to shave the articular surface of the glenoid. A conventional 3-hole template is introduced onto the guidewire that will allow to drill holes for the cancellous screws and the central peg. The base plate is then introduced and secured in place with the appropriate length cancellous screws. The metallic articular glenoid component is then snapped in and secured in place by means of securing and locking tabs. In a different embodiment, the metallic glenoid articular surface implant can be made from polyethylene or ceramic.

The metallic humeral component is then introduced through the anterior incision and threaded over the tip of the compression rod. Alignment grooves at the end of the central peg will assure that the sliding sleeve and outrigger are properly aligned for the insertion of the fixation screw. Said fixation screw penetrate through cortex providing better fixation than screw or other mechanical fixation means applied into weaker cancellous bone.

The polyethylene hemispherical head of the humerus is squeezed in through the anterior skin incision and snapped onto the metallic humeral component. The hole for fixation screw is then drilled, measured and taped. The fixation screw is then inserted in place through the front incision.

The drawing and detailed description of the present invention are not intended to limit the invention to the particular form as disclosed, but the invention is to cover all modifications, equivalent and alternatives falling within the spirit and scope of the present invention.

BRIEF DESCRIPTION OF THE DRAWINGS

The present invention will be better understood upon reading the following detailed description of the drawings, without limitation of the general inventive concept, method of implantation, instruments and non-limiting embodiments thereof, and on examining the attached drawings, in which:

FIG. 1 shows a perspective view of the humeral component.

FIG. 2 shows a perspective view of the external humeral head osteotomy guide.

FIG. 6 shows the centralizing device of the distal end of the humeral head cutting guide.

FIG. 7 shows a sectional view of the humeral implant.

DETAILED DESCRIPTION OF THE INVENTION

Figure 3:
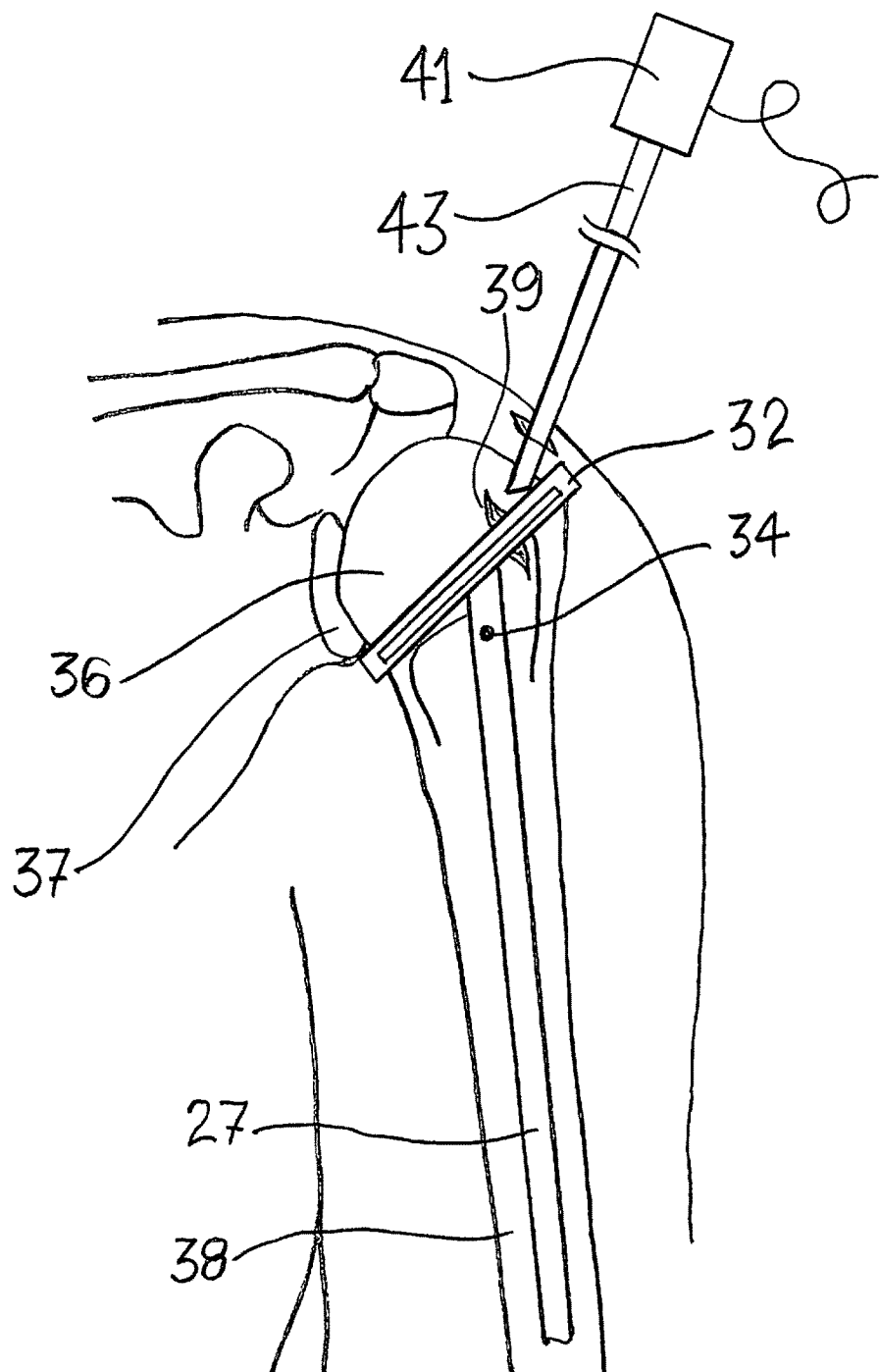
FIG. 3 shows a perspective view of the osteotomy guide transfixed with pin to humerus under arthroscopic guidance.

While the invention is susceptible to different changes and modifications, specific embodiments of the present invention are shown by way of example in the drawings and will be described herein in details.

Figure 17:
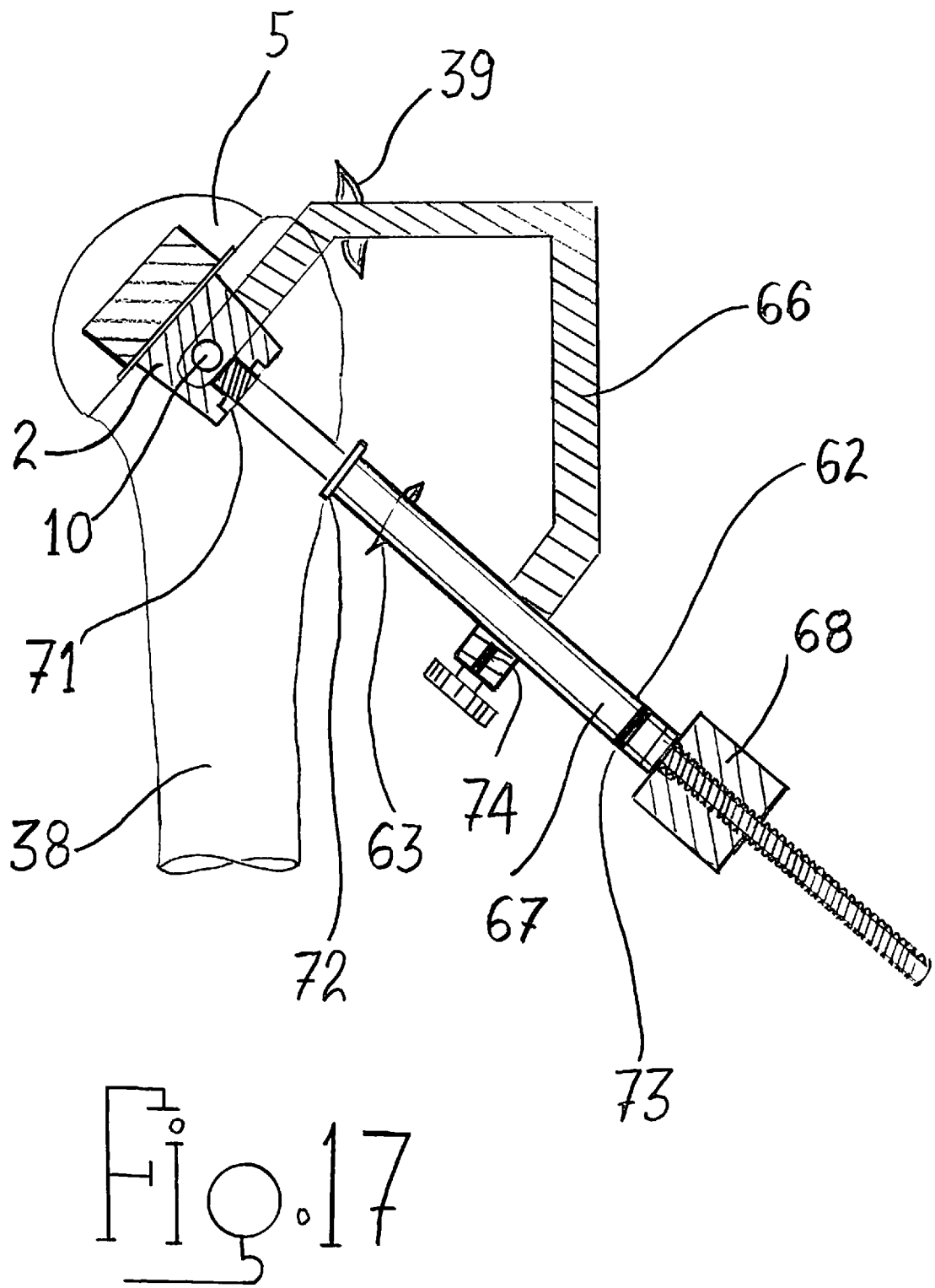
FIG. 17 shows sectional view of the humeral implant insert/compression rod and outrigger.
Figure 18:
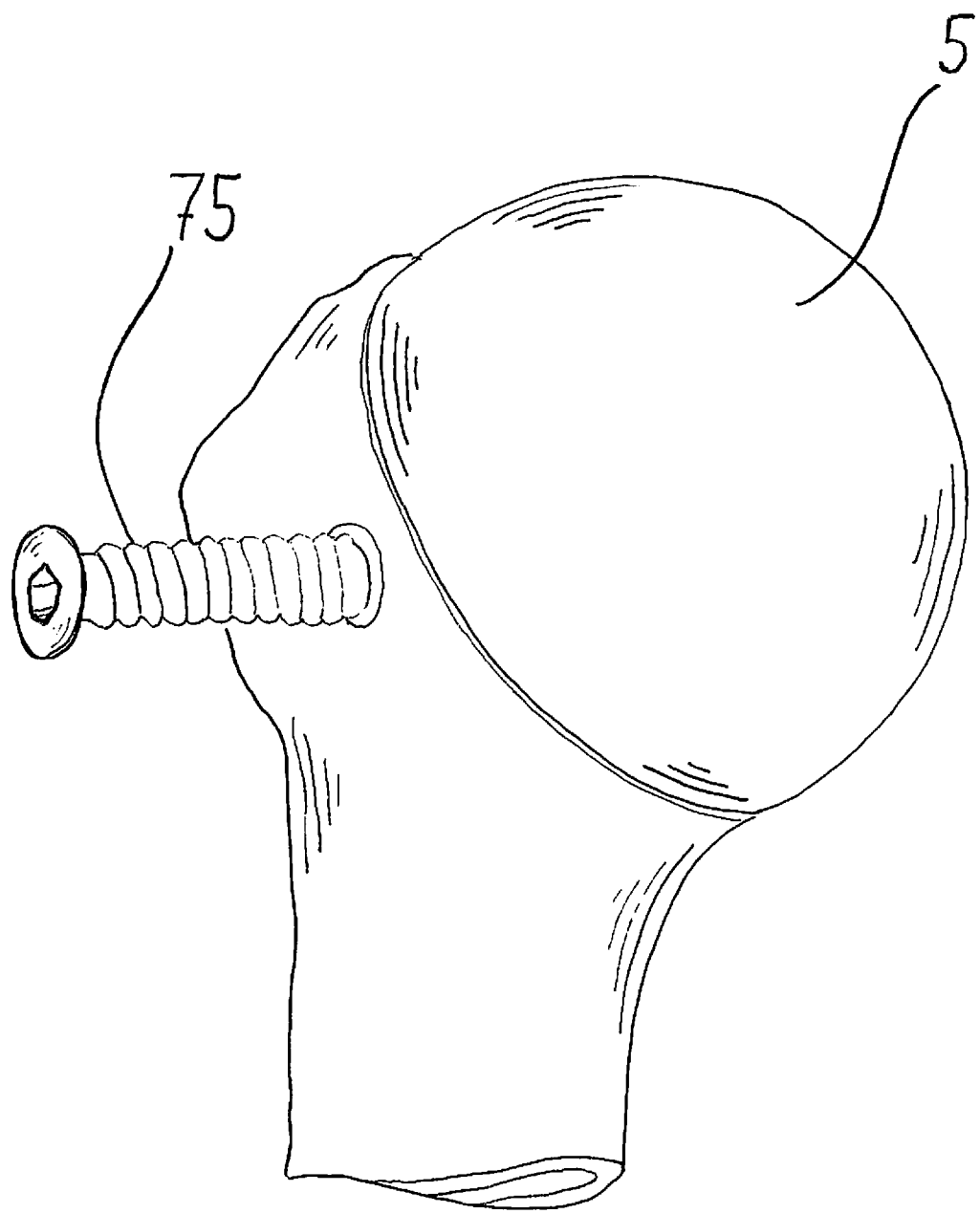
FIG. 18 is a flowchart of the insertion method of the present invention.
Figure 19:
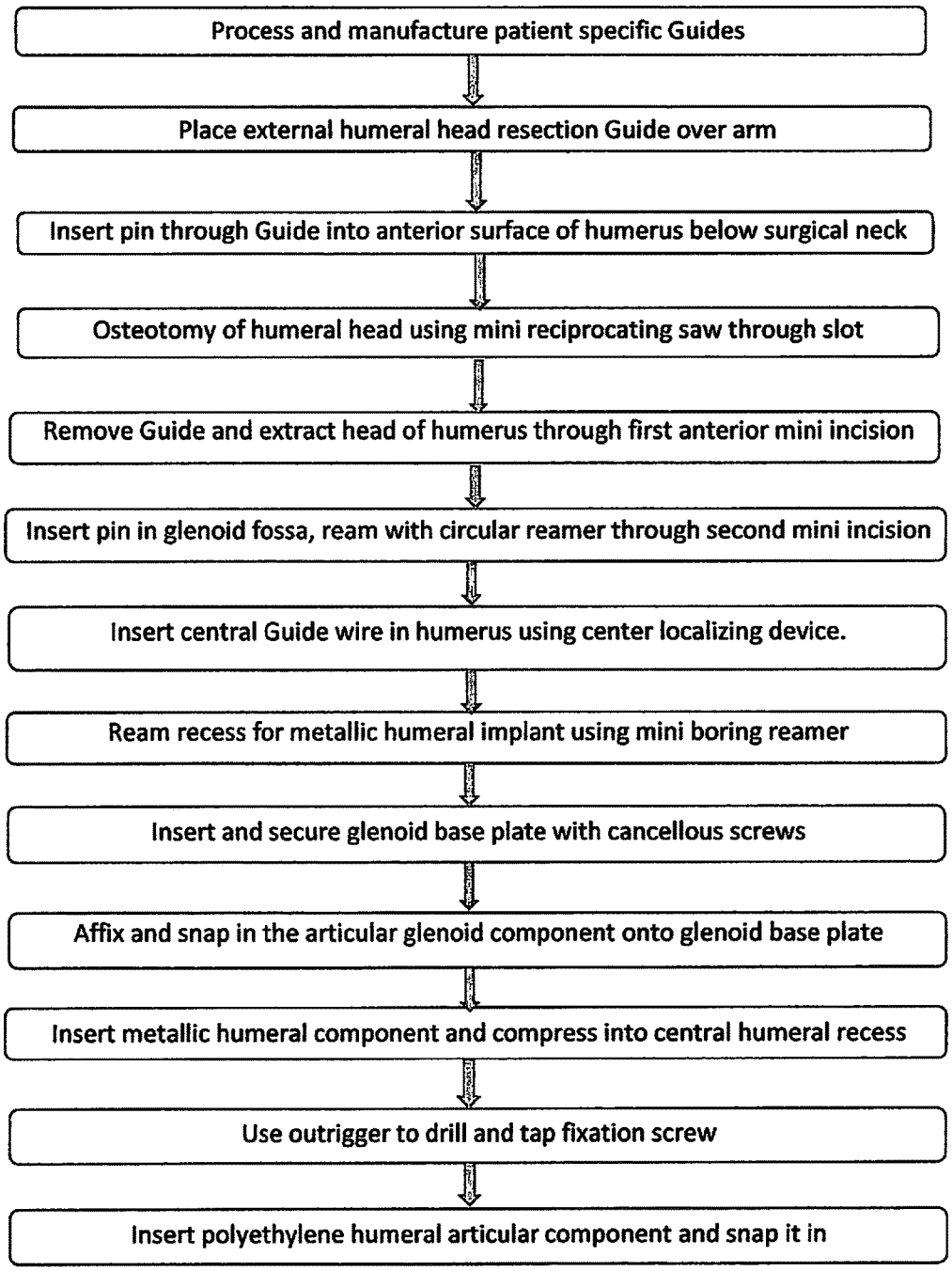
FIG. 19 is a perspective view of humeral implant and fixation screw inserted into proximal humerus.

Referring now to FIG. 1, which depict an embodiment of a humeral implant, which has a cup shape hemispherical articular polyethylene surface 5 and a metallic fixation portion 2. Said metallic portion comprises a central metallic tapered peg 2 at one end, which will be inserted into the humerus and the other end a cylindrical portion that will be slidingly inserted into the recess 6 situated on the flat surface of the polyethylene portion of the humeral head implant. At least two or more Locking tabs 8 will interlock into a circular groove 7 and securely attach the metallic cylinder into the polyethylene head. The metallic portion 2 of the central peg is slightly tapered at 2° to 5° for better retaining into the humeral bone. A circular disc 9 situated between the cylindrical and tapered portion is designed to reduce the flow of polyethylene under load and stop further penetration of the peg into the polyethylene. FIG. 7. Furthermore, a transverse cylindrical hole 10 passes through the middle section of the metallic peg 2 of the implant to receive a fixation screw after implant has been inserted and compressed in place in the proximal humerus. In addition, the end of the metallic peg 2 comprises a threaded hole 11 for receiving the threaded tip of the compression rod 67. FIG. 7 and FIG. 17.

In another embodiment of the present invention, the humeral head implant has a reverse geometry, where the humeral component has a hemispherical cupule articulating with a round hemispherical glenoid articular surface.

As mentioned earlier, the main purpose of the present invention is to provide a method for insertion of the humeral and glenoid components of a total shoulder using arthroscopic technique that will only require small stab wounds and significantly reduce skin incisions and surgical damage to the musculotendinous structures such as the subscapularis muscle.

Figure 4:
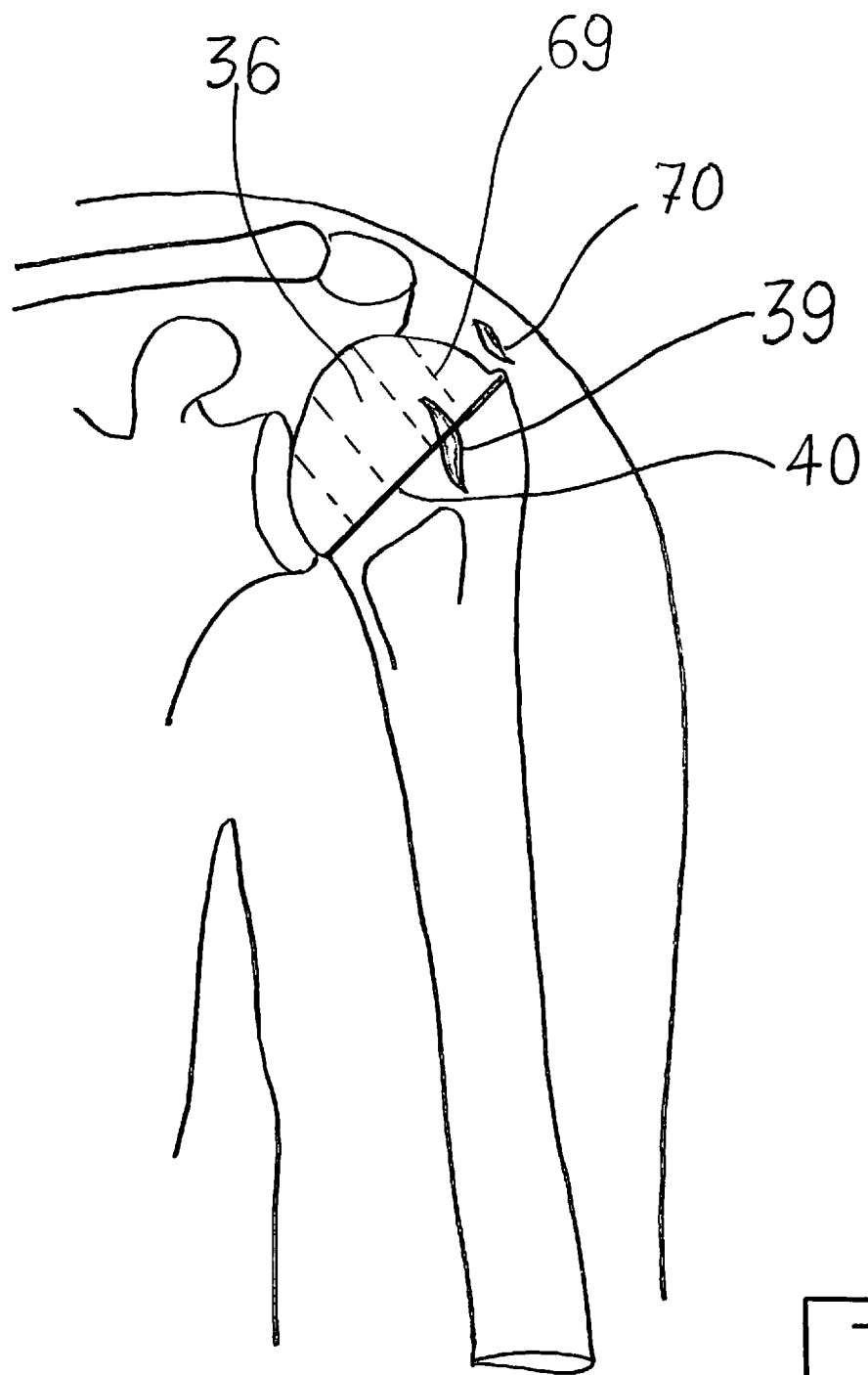
FIG. 4 shows a perspective view of the proximal humerus, entrance stab wounds and fragmental resection of the humeral head.
Figure 9:
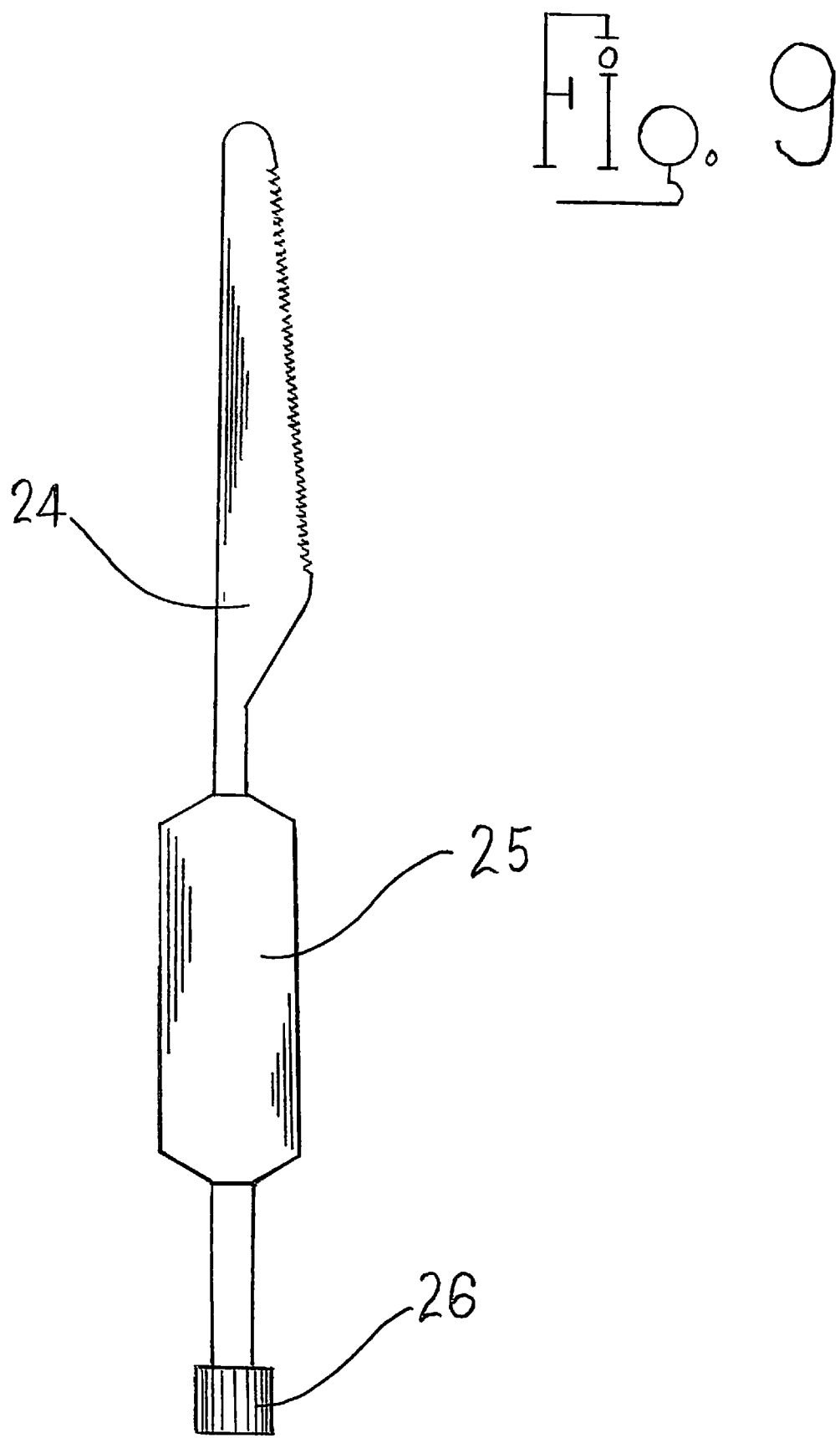
FIG. 9 shows a perspective top view of the mini reciprocating saw and guiding plate.

In order to accomplish this method, we initially remove the humeral head using an external cutting guide 27 applied over the anterior surface of the arm. A centering mechanism 28 will assure that the guide is centered over the bony landmarks of the elbow including the medial 29 and lateral 31 epicondylar bony prominences. FIG. 2. Proximally, the cutting guide is secured to the humerus using a pin 34. Said pin is inserted through small stab wound in the skin and its position is visually controlled by the operating surgeon using arthroscopic camera 41 attached to arthroscope 43 introduced anteriorly and superiorly through a stab wound 70. FIG. 3. The distal end of the guide is aligned over the anterior surface of the arm where medial and lateral expandable brackets 29 and 31 will assure that the guide is centrally located. FIG. 6. A first mini incision 39 is made anteriorly and a mini reciprocating saw blade FIG. 9 is introduced through slot of the cutting guide into the joint. said saw blade 24 having a guiding plate 25 and attached to a reciprocating conventional power driver via attachment 26. Guiding plate 25 will stabilize and ensure that saw blade 24 remains in the cutting plane at all time. The operating surgeon my encounter difficulty removing the humeral head because of deformity or size. Subsequently, segmental extraction can be achieved by cutting the head into several pieces or segments using the reciprocating saw FIG. 4. The smaller resected fragments 69 can be delivered through first incision 39.

Figure 5:
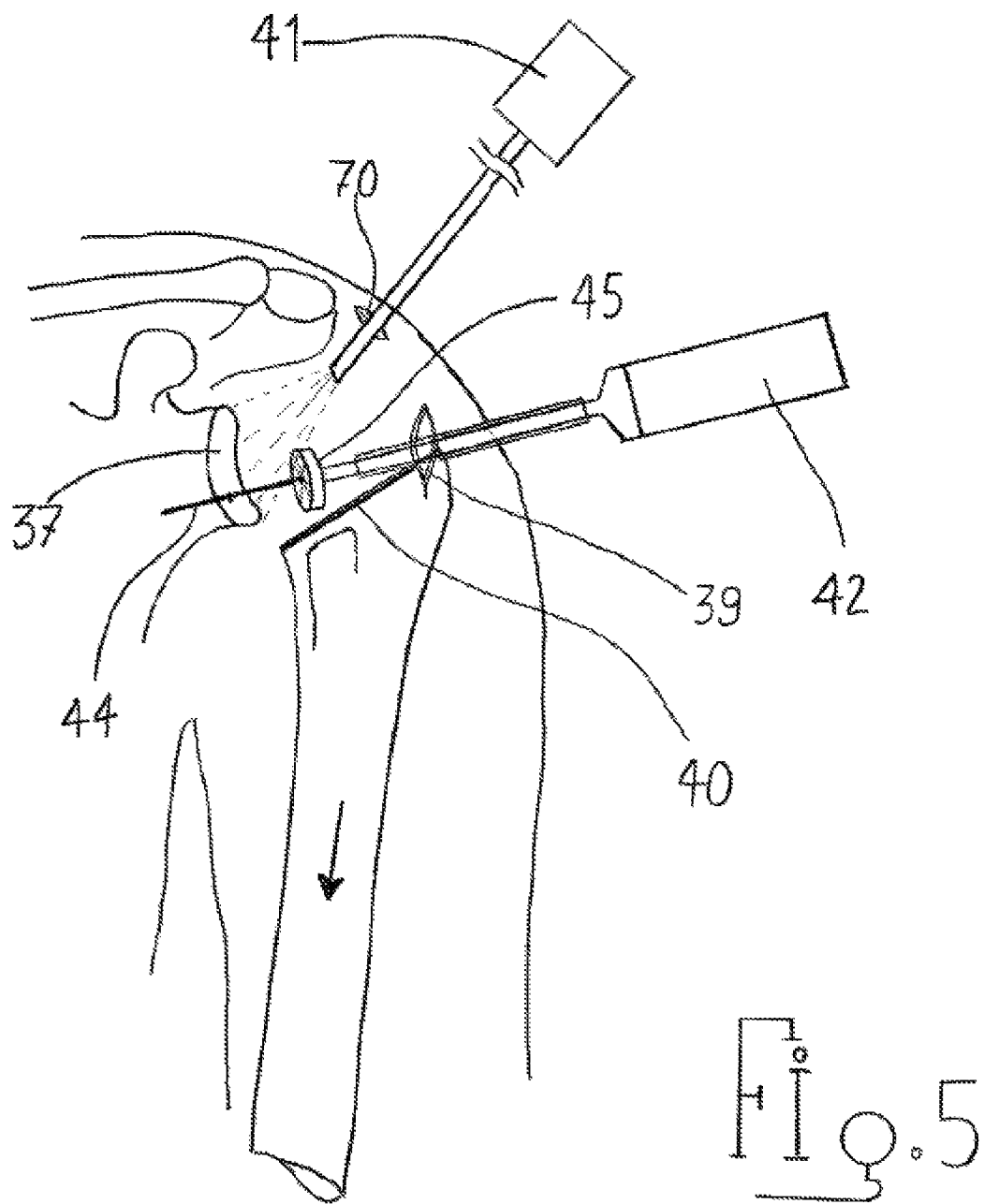
FIG. 5 shows power reamer of glenoid fossa after resection and removal of the humeral head.
Figure 8:
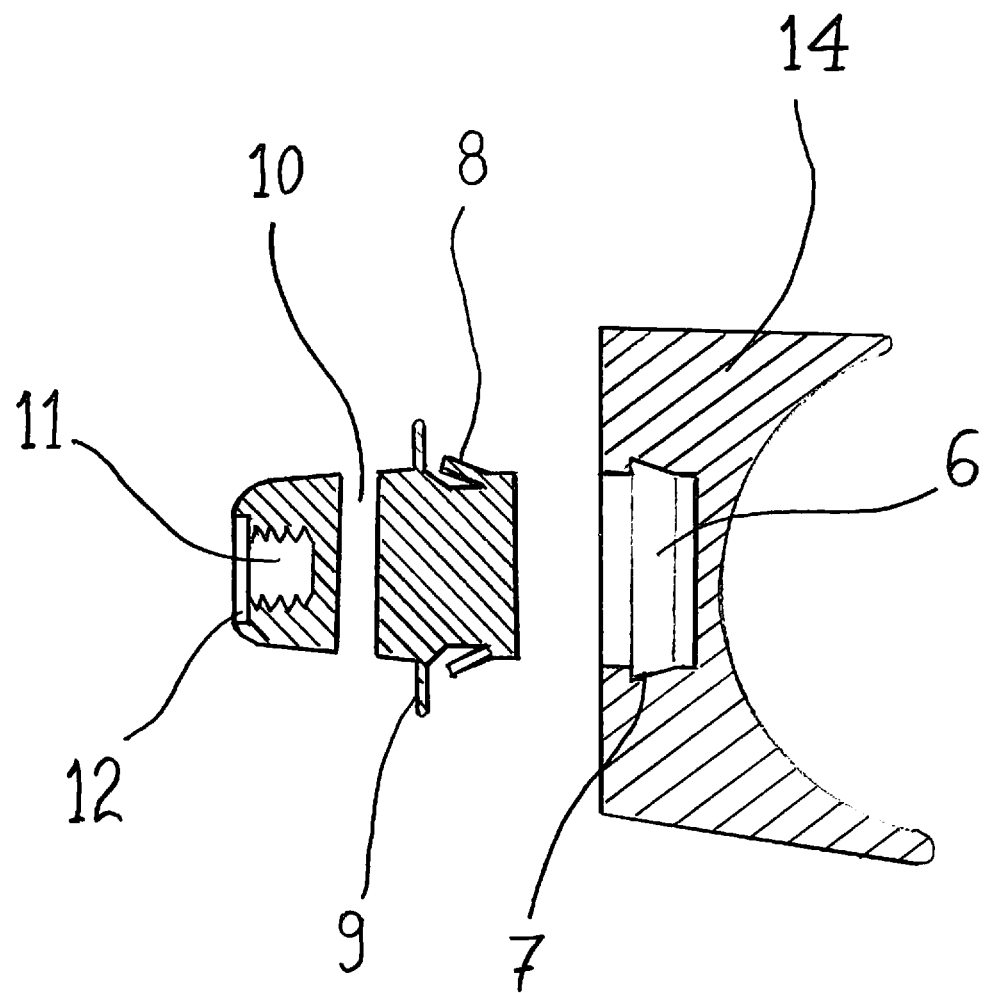
FIG. 8 shows another embodiment and sectional view of the reverse humeral implant.
Figure 15:
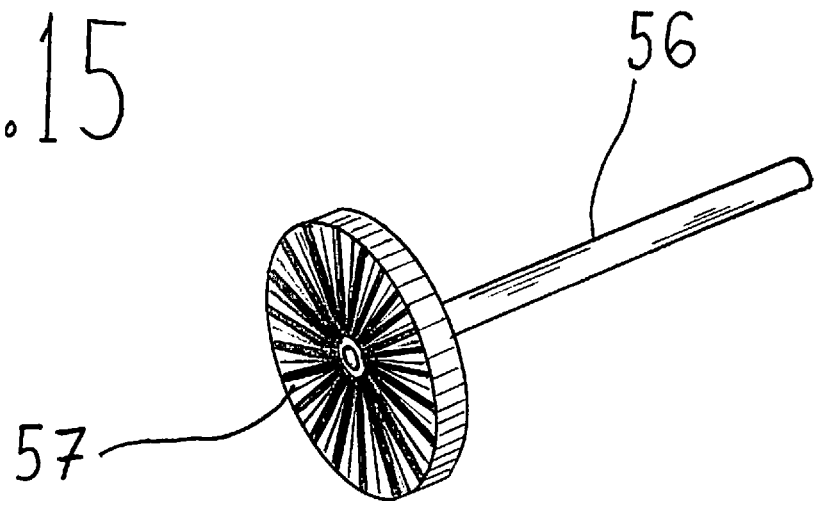
FIG. 15 shows the mini circular glenoid reamer.

Next step is to prepare the glenoid articular surface FIG. 5. In order to improve visualization of the glenoid cavity, the humerus can be pulled downward a rotated externally in order to increase the working space in the shoulder joint. A guide wire 44 is inserted in the glenoid surface 37 under direct arthroscope 41 visualization. A small circular reamer 45 attached to rotary power unit 42 is used to plane the surface FIG. 15. A second guide wire may be inserted adjacent to the planed surface in order to ream additional surface. Once the glenoid surface is prepared, conventional drill guide is inserted through first skin incision 39 and drill holes are made using long drill bits attached to external rotary power tool 42.

Figure 10:
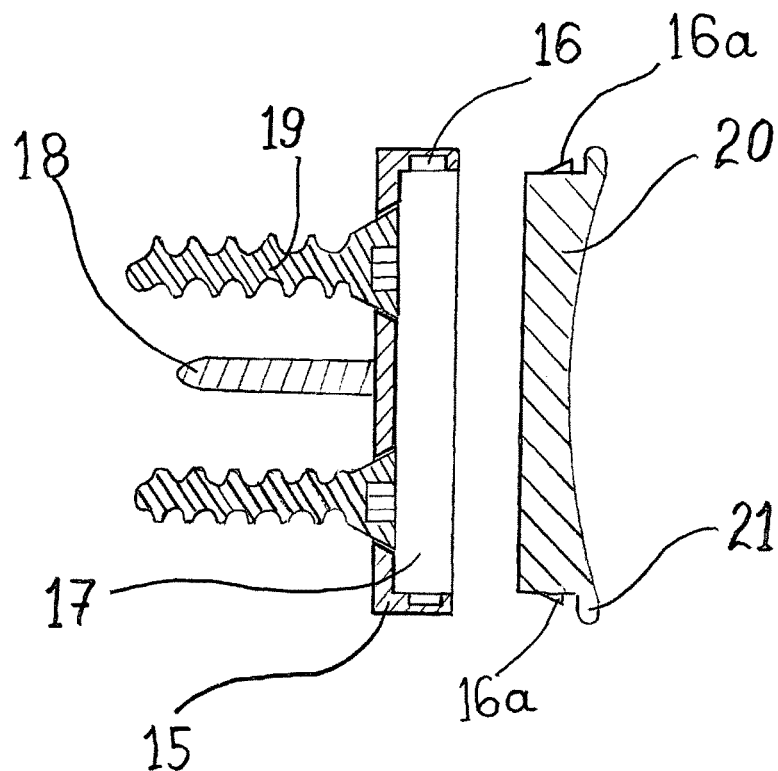
FIG. 10 shows a sectional view of the glenoid implant.
Figure 11:
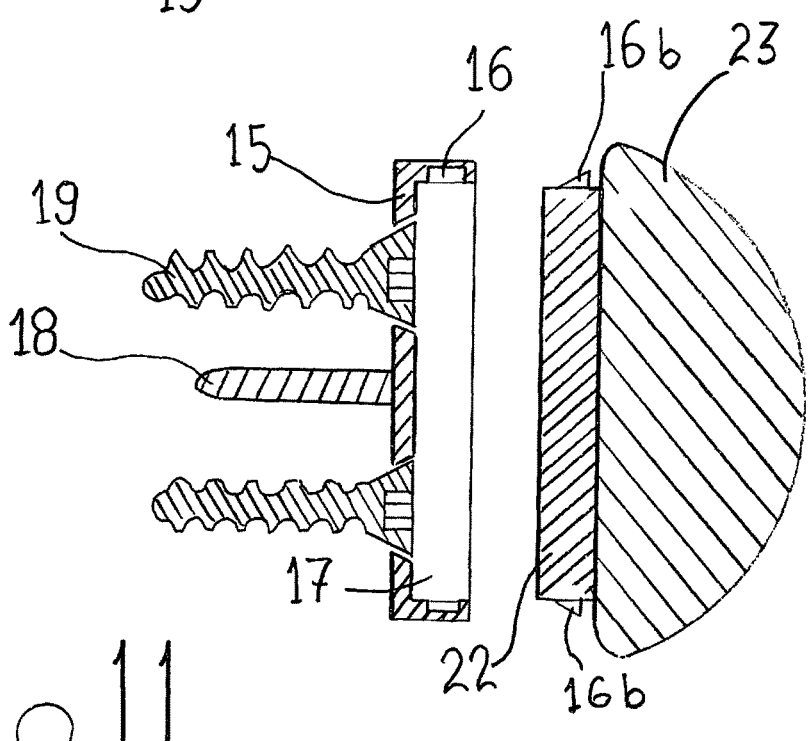
FIG. 11 shows a sectional view of the reverse glenoid implant.

The metallic glenoid plate 15 is then inserted and secured to the prepared glenoid surface under direct arthroscopic vision using two cancellous screws 19. A central post 18 will stabilize the plate during screw insertion. Subsequently, the glenoid articular implant 20 is inserted through skin incision 39 and snapped in securely in cavity 17 and secured by snaps and tabs 16 and 16a. FIG. 10 and FIG. 11.

In a different embodiment of the present invention the glenoid articular component of the reverse shoulder design has a convex hemispherical geometry FIG. 11. Again, the arthroscopic insertion method remains the same and the component is introduced through anterior incision wound 39 and snapped in the base plate and secured by snaps and tabs 16 and 16*b*.

Figure 12:
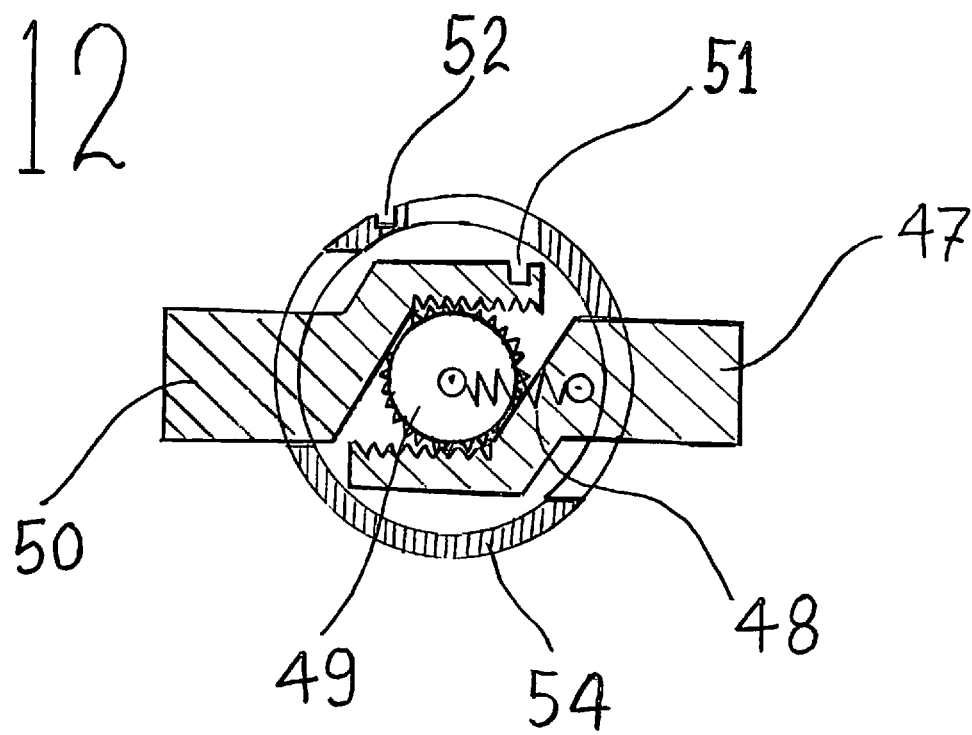
FIG. 12 shows top sectional view of the humeral center localizing device.
Figure 13:
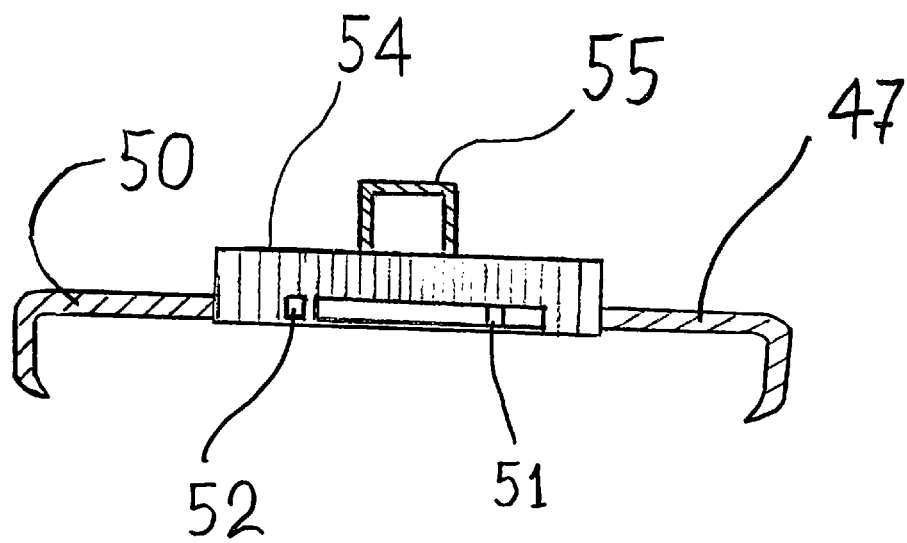
FIG. 13 shows side sectional view of the humeral center localizing device.
Figure 14:
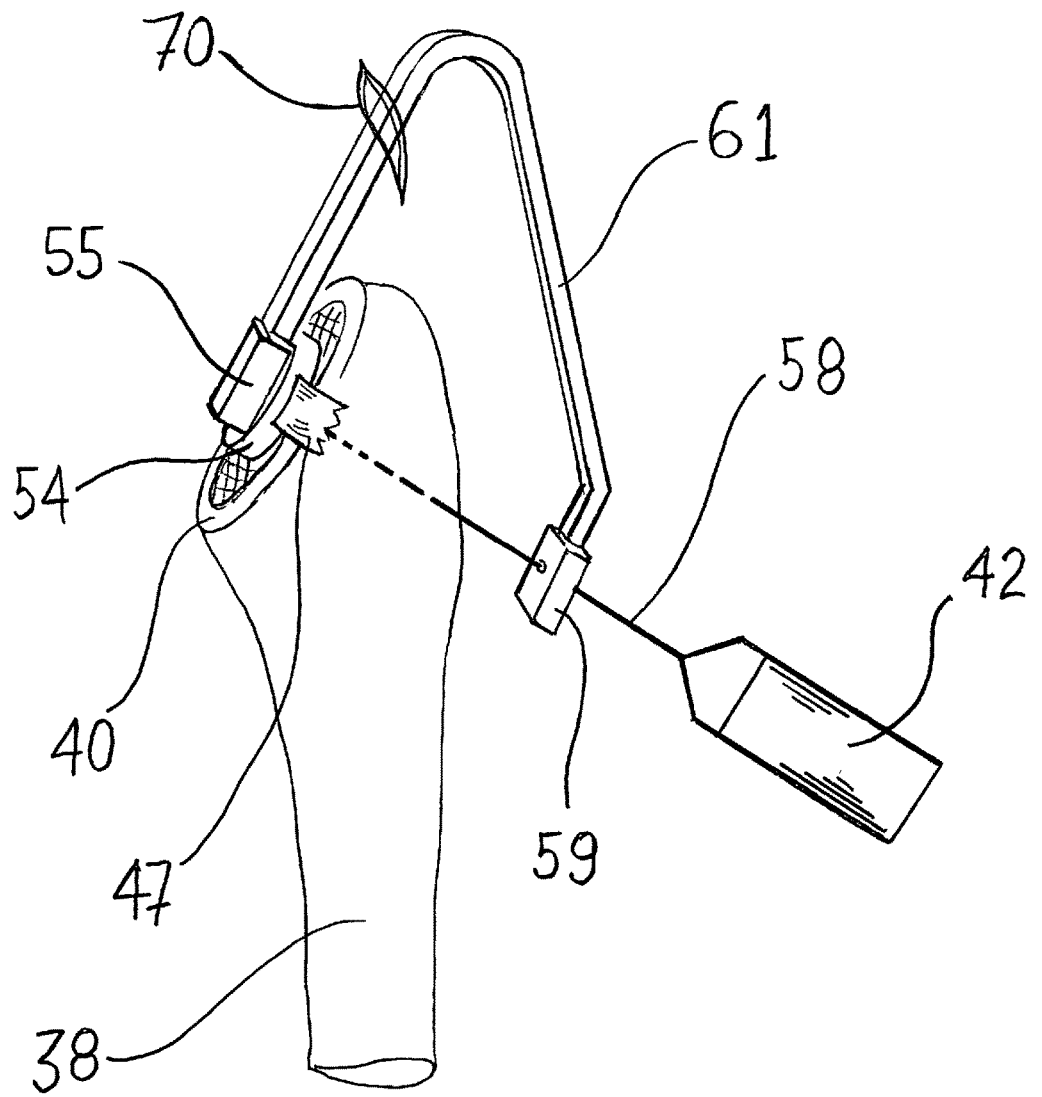
FIG. 14 shows a perspective view of the humeral center localizing device attached to the outrigger.
Figure 16:
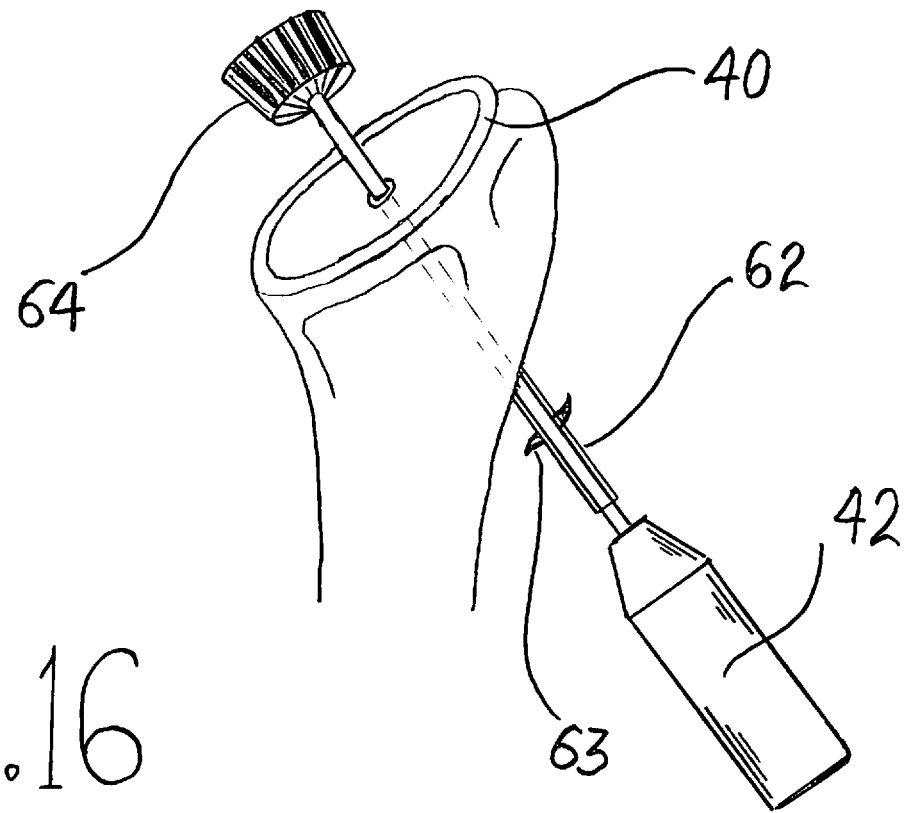
FIG. 16 shows boring reamer of the humeral implant.

The next step is preparing the humeral cut surface for insertion of the humeral component. A mechanical center locating device 54 is introduced through the anterior incision and placed onto the flat surface of the humerus. The appropriate centralized position of the device is checked directly by the surgeon through the arthroscope inserted superiorly through stab wound 70. The claws 50 and 47 are squeezed open using a surgical clamp where the two small recesses 51 and 52 are squeezed using the clamp FIG. 12 and, FIG. 13. Once the clamp is released the claws will be closed by the spring 48, thereby holding the device securely on the cut surface of the humerus FIG. 14. The outrigger is then attached to the centering device through the upper incision 70 and inserted into attachment channel 55. Said outrigger will facilitate the accurate insertion of the central guide wire 58 that will be used to insert the humeral bore reamer 64 and will also facilitate to accurately drill hole 10 and tap the proximal humerus for insertion of the fixation screw 75. A cannulated shaft 62 is inserted over the guidewire FIG. 16 and brought out in the center of the humeral cut surface. Said cannulated shaft is threaded at its proximal tip. A circular boring reamer 64 having centrally threaded portion will be introduce through main incision 39 and threaded onto the tip of cannulated shaft 62. The boring of the central portion of the humeral cut surface is arthroscopically observed. Subsequently, the metallic portion of the humeral implant is introduced through first incision 39 where the central peg is inserted in the bored central recess.

To accomplish compression of the implant into the recess, compression rod 67 and sliding cannulated sleeve 62 are introduced through lateral stab wound 63 and threaded into the implant's threaded recess 11. The sleeve 62 is advanced until it comes in contact with the lateral surface of the humerus and the alignment tabs 72 are pushed into the transverse alignment slot 72. Turning bolt 68 will compress the central peg 2 of the implant into the bored recess of the proximal humerus. The insertion of the locking fixation screw requires accurate drilling and tapping of the proximal humerus. To this end, outrigger 66 is attached to sliding sleeve 62 and advanced until marks 73 on the sliding sleeve is aligned with mark 74 on the outrigger. In doing so, the outrigger hole will be aligned with hole 10 in the implant peg. The fixation screw 69 is inserted and locked in place. The polyethylene component 5 is squeezed into the joint through the main incision 39 and locked onto the metallic component. Upon completion of the component insertion, the insertion holes made over the lateral surface of the humerus are plugged with bone graft.

What is claimed is:

1. A set of components configured for arthroscopically resecting a humeral head and glenoid fossa of a shoulder joint and replacing it with an implant, the set of components comprising:
    a stemless humeral head component affixable to a cylindrical metallic portion having a metallic tapered peg having a threaded recess, and a transverse hole;
    a glenoid component comprising a base plate and an articular insert;
    one or more cannulated shafts;
    a first outrigger having ends, and a hole for receiving a guide wire;
    a second outrigger having a hole for alignment with the transverse hole in the cylindrical metallic portion;
    a central recess boring reamer;
    a mechanical center locating device configured to be positioned against a flat surface of the humerus, the device comprising two claws attached to a spring which urges the claws together, and an attachment channel configured to be removably affixed to an end of the first outrigger;
    a cannulated sliding sleeve containing a threaded compression rod which has an end engageable with the threaded recess of the metallic tapered peg, the cannulated sliding sleeve removably affixable to the second outrigger.

2. The set of claim 1, wherein the stemless humeral component further comprises a hemispherical articular bearing surface having a flat back surface in its periphery and a central recess.

3. The set of claim 2, wherein the stemless humeral head component comprises a cylindrical metallic portion with flat surface at one end to be introduced into said a hemispherical articular bearing surface and a metallic tapered peg at the opposite end, wherein said metallic tapered peg extending laterally away from said flat surface, wherein said metallic tapered peg has a thin circular flange between said cylindrical and the tapered segments.

4. The set of claim 3, wherein the transverse hole is a cylindrical transverse hole for receiving a locking cortical screw.

5. The set of claim 3, wherein the hemispherical articular bearing surface is adapted to interlock with the flat portion of the metallic tapered peg.

6. The set of claim 3, wherein said central recess boring reamer is attached to a rotating shaft driven from a power unit for reaming a central recess for receiving said metallic tapered peg of the humeral head component.

7. The set of claim 2, wherein the articular bearing surface is constructed from a material selected from the group consisting of: ceramic, metal, metallic alloy and a composite plastic.

8. The set of claim 1, wherein said mechanical center locating device is configured to locate the center of a flat humeral cut surface.

9. The set of claim 1, which further comprises one or more reciprocating mini saw blades having a flat plate oriented in the cutting plane of the said reciprocating mini saw blade.

10. A set of claim 1,
    wherein the metallic tapered peg includes a thin circular flange between the cylindrical metallic portion and the metallic tapered peg portion,
    further wherein; the set comprises a compression knob engageable with the threaded rod at an end of the cannulated sliding sleeve.

11. The set of claim 1, wherein:
    the base plate of the glenoid component includes
    a circumferential rim and central peg and two holes configured for insertion of large cancellous fixation screws, and,
    an articular surface comprising a shallow cavity configured for articulation with the stemless humeral head, wherein said articular insert is seated into and locked into the base plate.

* * * * *